| United States Patent [19]
Sircar et al. | [11] Patent Number: 4,748,177 |
| [45] Date of Patent: May 31, 1988 |

[54] GUANINE DERIVATIVES

[75] Inventors: Jagadish C. Sircar; Catherine R. Brungardt, both of Ann Arbor, Mich.; Charles F. Schwender, Gladstone, N.J.

[73] Assignee: Warner-Lambert Company, Morris Plains, N.J.

[21] Appl. No.: 698,805

[22] Filed: Feb. 11, 1985

Related U.S. Application Data

[63] Continuation-in-part of Ser. No. 593,063, Mar. 26, 1984, abandoned.

[51] Int. Cl.⁴ .................... C07D 473/18; A61K 31/52

[52] U.S. Cl. .................................... 514/262; 544/276; 544/277

[58] Field of Search ................ 544/276, 277; 514/262

[56] References Cited

U.S. PATENT DOCUMENTS 3,900,474  8/1975  Ginger et al. ........................ 544/267
3,930,005  12/1975  Wojnar et al. ....................... 544/276

*Primary Examiner*—Nicholas S. Rizzo
*Attorney, Agent, or Firm*—Joan Thierstein

[57] ABSTRACT

Novel guanine derivatives are described as agents for treating autoimmune diseases as well as a method of manufacture and pharmaceutical compositions thereof.

18 Claims, No Drawings

GUANINE DERIVATIVES

This application is a continuation-in-part of application U.S. Ser. No. 593,063, filed Mar. 26, 1984, now abandoned.

BACKGROUND OF THE INVENTION

8-Aminoguanine, a compound known since the turn of the century, has been reported to have PNP-activity by R. Parks, et. al., in Biochem. Pharm., 31 (2), 163 (1982). A synthetic method for 8-amino-9-benzylguanine was discussed at the 16th Annual Graduate Meeting in Med. Chem., University of Michigan, Ann Arbor, Mich., however, the effect as a PNP inhibitor of a guanine substituent at N-9 was not reported and is unpredictable.

The present invention is related to novel guanine derivatives, particularly, guanines as having PNP- inhibiting activity.

SUMMARY OF THE INVENTION

The present invention relates to a compound of the formula

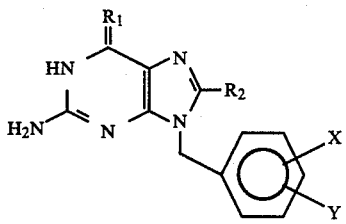

wherein $R_1$ is O or S; $R_2$ is bromine or NHR where R is hydrogen or $COR_5$, in which $R_5$ is alkyl of 1-4 carbon atoms, aryl or arylalkyl; X and Y are each independently halogen, alkyl of 1-4 carbon atoms, alkoxy of 1-4 carbon atoms, trifluoromethyl, hydroxy, $SO_nR_3$ in which n is 0,1,2 or 3 and $R_3$ is hydrogen or alkyl of 1-4 carbon atoms, $COOR_3$, CN, $NR_3R_4$ in which $R_4$ is hydrogen or alkyl of 1-4 carbon atoms, Y is also hydrogen, or a pharmaceutically acceptable acid addition or base salt thereof.

The present invention includes a method of manufacture, pharmaceutical compositions comprising an effective amount of a compound of the formula 1 with a pharmaceutically acceptable carrier, as well as a method of treatment of rejection in transplantation and of autoimmune diseases such as arthritis, systemic lupus erythematosus, inflammatory bowel diseases, juvenile diabetes, myasthenia gravis, multiple sclerosis, as well as viral infections and cancer by administering an effective amount of a compound of the formula 1 in unit dosage form.

The term "alkyl of 1-4 carbon atoms" means a straight or branched hydrocarbon chain up to 4 carbon atoms such as, for example, methyl, ethyl, propyl, isopropyl, butyl, isobutyl, sec-butyl or tertiarybutyl.

The term "aryl" includes an unsubstituted or substituted aromatic ring such as, phenyl or phenyl substituted by halogen, e.g., fluorine, chlorine, bromine, or iodine, alkyl of 1-4 carbon atoms, such as methyl or ethyl, hydroxy, alkoxy of 1-4 carbon atoms, such as methoxy or ethoxy, or trifluoromethyl.

The term "arylalkyl" means an aromatic ring attached to an alkyl chain of up to 4 carbon atoms, such as unsubstituted or substituted phenylethyl or benzyl where the substituents on the aromatic ring may be the same as defined above.

Pharmaceutically acceptable acid addition salts are those derived from inorganic acids such as hydrochloric, sulfuric and the like, as well as organic acids such as methanesulfonic, toluenesulfonic, tartaric acid, and the like. These salts may be prepared by standard methods known in the art.

Pharmaceutically acceptable base salts are those derived from inorganic bases such as sodium hydroxide, potassium hydroxide or ammonium hydroxide or organic bases such as arginine, N-methyl glucamine, lysine and the like. These salts may also be prepared by standard methods known in the art.

A preferred embodiment of the present invention is a compound of formula 1 wherein $R_1$ is O or S; $R_2$ is bromine; Y is hydrogen and X and Y are each independently halogen, alkyl of 1-4 carbon atoms, alkoxy of 1-4 carbon atoms, hydroxy or trifluoromethyl, or a pharmaceutically acceptable acid addition or base salt.

Another preferred embodiment of the present invention is a compound of formula 1 wherein $R_1$ is O $R_2$ is bromine or $NH_2$; Y is hydrogen and X and Y are each independently fluorine, chlorine, methyl, methoxy, hydroxy or trifluoromethyl, or a pharmaceutically acceptable acid addition or base salt.

Particular embodiments of the present invention include:
8-bromo-9-[(4-methylphenyl)methyl]guanine;
8-bromo-9-[(4-chlorophenyl)methyl]guanine;
8-bromo-9-[(4-methoxyphenyl)methyl]guanine;
8-bromo-9-[(4-fluorophenyl)methyl]guanine;
8-bromo-9-[(3,4-dichlorophenyl)methyl]guanine;
8-amino-9-[(4-chlorophenyl)methyl]guanine;
8-amino-9-[(4-fluorophenyl)methyl]guanine;
8-amino-9-[(2-methoxyphenyl)methyl]guanine;
8-amino-9-[(4-methoxyphenyl)methyl]guanine;
8-amino-9-[(4-methylphenyl)methyl]guanine;
8-bromo-9-[(2-methoxyphenyl)methyl]guanine;
8-bromo-9-[(3-methoxyphenyl)methyl]guanine;
8-bromo-9-[(3-chlorophenyl)methyl]guanine;
8-amino-9-[(4-dimethylaminophenyl)methyl]guanine;
8-amino-9-[(2-dimethylaminophenyl)methyl]guanine; and
8-bromo-9-[(2,6-dimethoxyphenyl)methyl]guanine.

The compounds of the formula 1 where $R_2$ is bromine are not only useful pharmacologically but are also useful as intermediates for preparing certain compounds of the present invention where $R_2$ is amino or aminoalkanoyl.

The compounds of formula 1 may be prepared according to the following scheme:

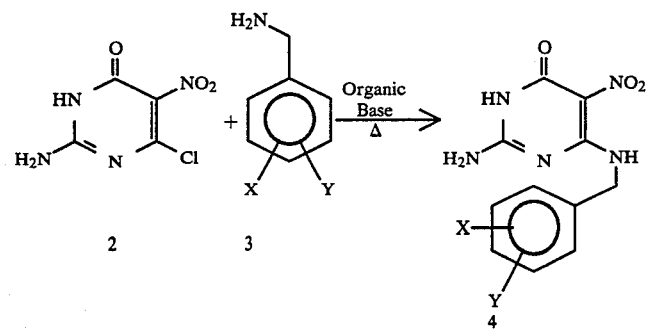
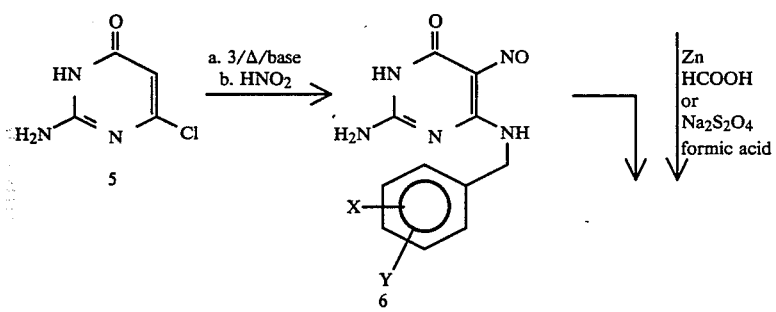
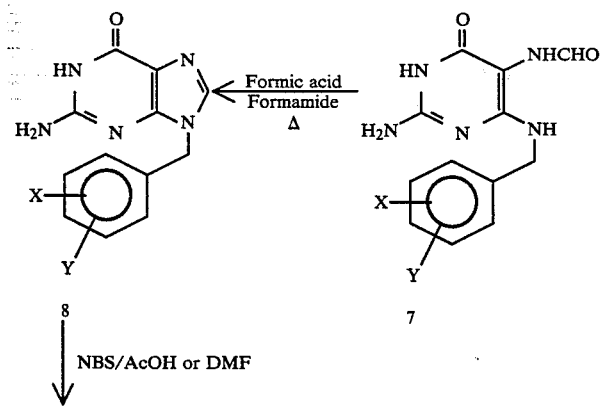
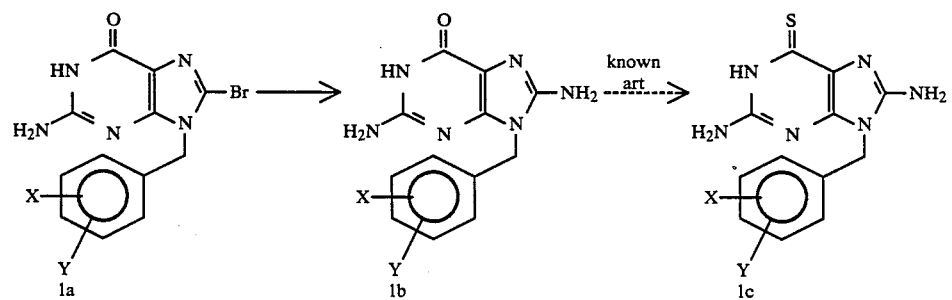

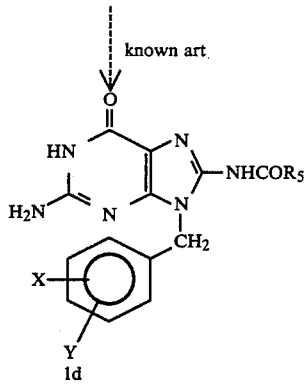

Starting materials of formula 8 above may be prepared by reacting 2-amino-6-chloro-4-hydroxy-5-nitropyrimidine, the compound of formula 2 described in J. Chem. Soc., 1963, p. 4186, with the appropriate benzylamine of formula 3 in the presence of an organic base at elevated temperatures. The resulting compound of the formula 4 is then treated with zinc and formic acid or sodium dithionite and formic acid followed by further treatment with formic acid and formamide at elevated temperatures to afford the compound of formula 8.

Alternatively, starting materials of formula 8 may be prepared according to a modified method of C. W. Noell and R. K. Robins in J. Med. Chem., 5, 558, (1962) starting with a compound of the formula 5 which is reacted with an appropriate benzylamine, 3, then with nitrous acid to form the 5-nitrosopyrimidine, 6, which is reduced and ring closed by treatment with sodium dithionite, formic acid and formamide as described above.

Treatment of a compound of formula 8 with N-bromosuccinimide in an organic solvent such as acetic acid, DMF, etc. produces a compound of formula 1a which when treated with hydrazine hydrate gives the hydrazine or directly the 8-amino derivative of formula 1b. The reaction of the 8-bromo compound with hydrazine may or may not proceed entirely to the 8-amino compound. Thus when the 8-hydrazine compound is obtained, it may be further reacted with Raney nickel to allow the reduction to go to completion and afford the desired 8-amino compound. Compounds of formula 1b may be further converted by known methods to provide $R_5$ substituents of formula 1d or, where $R_1$ is O converting said compound to a compound of formula 1c where $R_1$ is S by known means.

The compounds of the present invention have been shown to exhibit significant enzyme inhibition activity and cytotoxic activity. In the purine nucleoside phosphorylase (PNP-4) enzyme assay, total inhibition was achieved at a concentration less than about 300 micromoles on certain compounds. PNP-4 activity was measured radiochemically by measuring the formation of [$^{14}$-C]-hypoxanthine from [$^{14}$-C]-inosine [Biomedicine, 33, 39 (1980)] using human erythrocyte as the enzyme source. The same compounds also were found by a standard test [Science, 214, 1137, (1981)] to be selectively cytotoxic for T-cells in the presence of 2'-deoxyguanosine at a similar concentration range. For example, 8-amino-9-[(4-methylphenyl)methyl]guanine is selectively cytotoxic to T-cells at a concentration of about 3.1 $\mu$M in the presence of 10 $\mu$M of 2'-deoxyguanosine. Similarly, 8-amino-9-[(4-methoxyphenyl)methyl]guanine is selectively cytotoxic to T-cells at concentration of about 1.1 $\mu$M in the presence of 10 $\mu$M of 2'-deoxyguanosine. On the other hand, these compounds were nontoxic to B-cells in the presence or absence of the same amount of 2'-deoxyguanosine. Since T-cells play a central role in immune response, use of the compounds of the invention is contemplated for the immunoregulation of rejection in transplantation and autoimmune disease such as rheumatoid arthritis, systemic lupus erythematosus, inflammatory bowel disease, cancer, juvenile diabetes, myasthenia gravis, multiple sclerosis, and viral diseases. The present invention thus includes compositions containing a compound of formula 1 in treating disease such autoimmune disease characterized by abnormal immune response in warm-blooded animals. According to this aspect of the invention, the properties of the compounds of the invention are utilized by administering to a warm-blooded animal an effective amount of a pharmaceutical composition containing as the active ingredient at least about 0.1 percent by weight, based on the total weight of the composition of at least one such compound of the invention.

Pharmaceutical compositions of the invention can be formulated in any suitable way, preferably with an inert carrier for administration orally, parenterally, ophthalmically, topically, or by suppository.

For example, the compounds of the present invention are formulated into dosage forms such as tablets or syrups by blending with an inert pharmaceutical carrier such as lactose or simple syrup by methods well known in the art. For injectionable dosage forms, they are formulated with vehicles such as water, peanut oil, sesame oil, and the like. In these dosage forms, the active ingredient is from about 0.05 grams to 0.5 grams per dosage unit.

The present invention is further illustrated by way of the following examples.

EXAMPLE 1

9-[(4-Methoxyphenyl)methyl]guanine

4-Methoxybenzylamine (13.7 g, 0.1 mole) is added to a suspension of 2-amino-6-chloro-4-hydroxy-5-nitropyrimidine (9.53 g, 0.05 mole) [A. Stuart and H. C. S. Wood, J. Chem. Soc., 4186 (1963)] in isopropanol (500 ml). The resulting solution is refluxed overnight during which time 2-amino-4-hydroxy-6-(4-methoxybenzylamino)-5-nitropyrimidine started to crystallize out. The reaction mixture is cooled in an ice bath and the product (17.2 g) filtered, washed with methanol and air dried.

The crude nitro-pyrimidine (17.2 g) from above is suspended in formamide (100 ml) and 90% formic acid (50 ml) and the suspension is warmed to 70° C. in a waterbath. Sodium dithionite is carefully added to the warm suspension over a period of 45 minutes. The reaction mixture is stirred at 70°–80° C. until the foaming subsided and then boiled for 20 minutes. The reaction mixture is diluted with hot water (1000 ml) and then boiled for an additional 20 minutes, treated with charcoal, filtered through celite and cooled when the formamidopyrimidine derivative crystallized out.

The above product is resuspended in formamide (30 ml) and formic acid (6 ml) and is refluxed at 175°–180° C. for 4 hours, poured onto ice water and filtered. The crude guanine is collected and then dissolved in boiling 1N HCl (400 ml), treated with charcoal, and filtered through celite, and basified with NH4OH solution. The crude guanine is purified one more time by redissolving in hot NaOH, treating with charcoal and then reprecipitating with acetic acid. The resulting precipitate is filtered, washed with water and methanol and dried to give 5.75 g of the desired product, mp >300° C.

EXAMPLE 1A

9-[(4-dimethylaminophenyl)methyl]guanine

A suspension of 2-amino-6-chloro-4-hydroxy-5-nitropyrimidine (9.4 g, 49 mmol) [A. Stuart and H. C. S. Wood, J. Chem. Soc., 4, 186 (1963)] and p-dimethylaminobenzylamine.2 HCl (11 g, 49 mmol) in methanol (400 ml), and triethylamine (25 ml, 0.18 mol) is stirred at room temperature for two days. The yellow precipitate (13.4 g) is collected by filtration and washed with methanol. The product from above is dissolved in 95–97% formic acid (900 ml) under a nitrogen atmosphere. Zinc dust (60 g) is added in ten portions and the reaction mixture is stirred for 30 minutes without cooling. The reaction mixture is filtered through celite and the filtrate concentrated to 50 ml under vacuum (bath temperature <35° C.). The residue is taken up in water (400 ml) and the crude N-formyl derivative is precipitated by basifying the solution with ammonium hydroxide solution. The crude N-formyl derivative (9.1 g) is collected by filtration, washed with water (1000 ml), and dried over P2O5.

The crude product from above is resuspended in dry DMF (75 ml) and potassium carbonate (15 g) is added. The reaction mixture is refluxed overnight and then cooled and poured into ether (1000 ml). The precipitate is collected by filtration and washed with water to remove the potassium carbonate. The product is recrystallized from 10% DMF/H2O (4000 ml) to give 9-(4-dimethylaminophenyl)methyl guanine (6.5 g) mp >255° C. dec.

SCHEME II

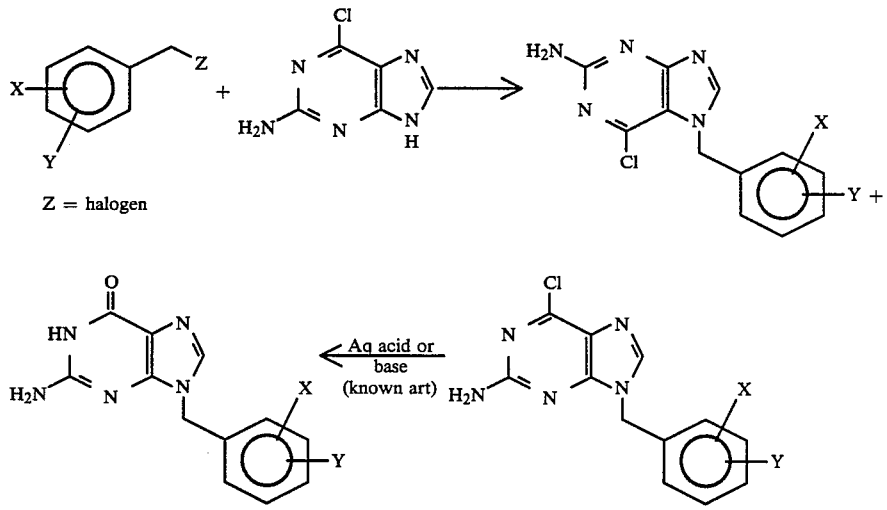

Z = halogen

This scheme is exemplified in the following Examples 1B and 1C.

EXAMPLE 1B 2-amino-9-[(4-carbomethoxyphenyl)methyl]-6-chloropurine

A mixture of 2-amino-6-chloropurine (5 g, 0.029 mol), 4-(bromomethyl)benzoic acid methyl ester (6.7 g, 0.029 mol), and potassium carbonate (4.0 g, 0.029 mol) in dry DMF (75 ml) is stirred at room temperature for three days. The reaction mixture is filtered and the filtrate is evaporated to near dryness under vacuum. Water is added and the precipitate is collected by filtration to give a mixture of 7- and 9-substituted products (10.5 g). A sample of pure 9-isomer, i.e., 2-amino-9-[(4-carbomethoxyphenyl)methyl]-6-chloropurine, (mp=150°–155° C. softens, 183°–185° C. melts) is prepared by chromatography on silica gel with 5% methanol/chloroform as the eluting solvent to separate it from the slower moving 7-isomer.

EXAMPLE 1C

9-[(4-carboxyphenyl)methyl]guanine

A solution of 2-amino-9[(4-carbomethoxy)phenyl)-methyl]-6-chloropurine (100 mg, 0.31 mmol) in 1 N HCl is refluxed for five hours. The product is collected by filtration, and dried to give the desired guanine derivative, 9-[(4-carboxyphenyl)methyl]guanine (70 mg), mp >300° C.

EXAMPLE 2

The procedure described in Example 1 is repeated to prepare 9-(phenyl)methylguanine, starting from 2- amino-6-chloro-4-hydroxy-5-nitropyrimidine and benzene methanamine.

In a manner also as described in Example 1 using the appropriate starting materials the following compound was prepared.

9-[(2,6-Dimethoxyphenyl)methyl]guanine, mp>300° C. (dec).

EXAMPLE 3

9-[(4-Chlorophenyl)methyl]guanine

This is prepared according to the modified procedure of C. W. Noell and R. K. Robins (J. Med. Chem., 5, 558 (1962). 2-Amino-6-chloro-4-pyrimidinol monohydrate (10 g, 0.06 mole) is suspended in methoxyethanol (20 ml) and 4-chlorobenzenemethanamine (25 g, 0.18 mole) is added to the suspension. The resulting solution is refluxed for 4 hours and the hot solution is poured into 300 ml of water and ice. The solution is diluted with acetic acid (100 ml) and then treated with a solution of sodium nitrite (20 g) in water (100 ml). The reaction mixture is stirred at room temperature for two hours and the resulting red solid is collected by filtration and washed with water.

The crude nitrosopyrimidine is then reduced with sodium dithionite (13 g) in formamide (100 ml) and formic acid (50 ml) at 70° C. and then boiled for 15 minutes. The reaction mixture is diluted with water (400 ml) and boiled for an additional 30 minutes, filtered through Celite and allowed to crystallize in the refrigerator. The crude N-formyl derivative (11.0 g) is collected by filtration and then cyclized with formic acid (6 ml) and formamide (35 ml) at 175°–180° C. for 3 hours. The hot reaction mixture is poured into ice water (250 ml) to give the crude guanine which is then purified by dissolving in boiling 1 N HCl, treating with charcoal and then precipitating with ammonium hydroxide. The crude guanine is then dissolved in hot 1 N NaOH solution, treated with charcoal, filtered and the filtrate acidified with acetic acid to give the pure product (4.5 g); mp>300° C.

EXAMPLE 4

The procedure described in Example 3 is repeated to prepare the following 9-(substituted phenyl)methylguanines, starting from 2-amino-6-chloro-4-pyrimidinol monohydrate and the appropriate substituted benzene methanamines in each case:

9-(4-methylphenyl)methylguanine, mp>300° C.;
9-(3,4-dichlorophenyl)methylguanine, mp>300° C.;
9-(4-fluorophenyl)methylguanine, dec>280° C.;
9-[(2-methoxyphenyl)methyl]guanine, mp 303°–305° C. (dec);
9-[(3-methoxyphenyl)methyl]guanine, mp 283°–287° C. (dec); and
9-[(3-chlorophenyl)methyl]guanine, mp>300° C. (dec).

EXAMPLE 5

8-Bromo-9-[(4-chlorophenyl)methyl]guanine

N-Bromosuccinimide (1.3 g, 7.3 mmol) is added to a suspension of 9-(4-chlorophenyl)methylguanine (1.5 g; 5.4 mmol), Example 3, in glacial acetic acid (100 ml) and the mixture is stirred for 20 hours at room temperature. The solution is poured into water (400 ml) and the resulting precipitate is filtered, washed with water and methanol and dried. Yield: 1.0 g; mp>300° C.

EXAMPLE 6

The procedure described in Example 5 is repeated to prepare the following 8-bromo-9-[(substituted phenyl)methyl]guanines, starting from appropriate 9-(substituted phenyl)methylguanines in each case:

8-bromo-9-[(4-methoxyphenyl)methyl]guanine; mp 256°–260° C. (dec.);
8-bromo-9-[(4-methylphenyl)methyl]guanine; mp 269°–271° C. (dec.);
8-bromo-9-[(4-fluorophenyl)methyl]guanine, mp>300° C.;
8-bromo-9-[(phenyl)methyl]guanine, mp>265° C. (dec.); and 8-bromo-9-[(3,4-dichlorophenyl)methyl]guanine, mp 295°–296° C. (dec.).

The procedure described in Example 5 is repeated using DMF as solvent to prepare the following 8-bromo-9-[(substituted phenyl)methyl guanines, starting from appropriate 9-(substituted phenyl)methyl guanines in each case:

8-bromo-9-[(2-methoxyphenyl)methyl]guanine, mp 286°–287° C. (dec);
8-bromo-9-[(3-methoxyphenyl)methyl]guanine, mp 296°–298° C. (dec);
8-bromo-9-[(3-chlorophenyl)methyl]guanine, mp 305°–308° C. (dec); and
8-bromo-9-[(2,6-dimethoxyphenyl)methyl]guanine, mp>250° (dec).

EXAMPLE 7

8-Amino-9-[(4-chloroHhenyl)methyl]guanine

A mixture of 8-bromo-9-[4-chlorophenyl)methyl]guanine (1.0 g; 2.82 mmol) and 54% aqueous hydrazine (100 ml) is heated to reflux for 90 hours. The clear solution is cooled and carefully adjusted to pH 11 with acetic acid, diluted with water and cooled. The crystalline solid is filtered, washed with water and methanol and dried. Yield: 0.4 g, mp>300° C.

In some experiments, the crude product is contaminated with the 8-hydrazine compound due to incomplete reduction. The crude product is then reduced further with Raney-nickel in alcohol or isopropanol-water.

EXAMPLE 7A

8-Amino-9-[(4-dimethylaminophenyl)methyl]guanine, dihydrochloride

To a solution of 9-[(4-dimethylaminophenyl)methyl]guanine (5 g) in acetic acid (100 ml) and water (10 ml) is added 2.2 g of 30% aqueous hydrogen peroxide and the reaction mixture is heated at 55° C. for six hours. The solution is concentrated to a thick oil and the desired amine oxide is separated from any remaining starting material by reverse phase chromatography ($C_{18}$ - reverse phase silica, 20% methanol/$H_2O$). The amine oxide from above (3.05 g) is dissolved in methanol (100 ml) and treated with N-bromosuccinimide (2.1 g) overnight. Water (10 ml) is added and the reaction mixture is stirred for 30 minutes at room temperature and then evaporated to dryness under vacuum. The residue is dissolved in 10% aqueous acetic acid (250 ml) and sodium dithionite (1.8 g) is added at 0°–5° C. The reaction mixture is stirred for one hour and the solid (1.58 g) isolated by filtration. The crude 8-bromo compound (1.58 g) from above is suspended in 54% aqueous hydrazine (100 ml) and refluxed for two days under a nitrogen atmosphere. The product (mixture of 8-amino and 8-hydrazino) which crystallized out after one day at room temperature (0.69 g) is treated with Raney-nickel (3 g) in refluxing 2:1 isopropanol:water for eight hours. The reaction mixture is filtered through Celite and evaporated to dryness. An analytical sample (90 mg) is prepared by triturating the residue with hot DMF and collecting the insoluble 8-amino purine derivative by filtration, and then converting it to the ·2 HCl salt which is recrystallized from ethanol/acetone, mp>150° C. dec.

EXAMPLE 7B

The procedure described in Example 7A is repeated to prepare 8-amino-9-[(2-dimethylaminophenyl)methyl]guanine, dihydrochloride, mp>190° (dec).

EXAMPLE 8

The procedure described in Example 7 is repeated to prepare the following 8-amino-9-[(substituted phenyl)methyl]guanines or the hydrochloride salts of 8-amino-9-[(substituted phenyl)methyl]guanines, starting from appropriate 8-bromo-9-[(substituted phenyl)methyl]guanines:

8-amino-9-[(4-fluorophenyl)methyl]guanine HCl salt, mp>290° C. (dec);
8-amino-9-[(4-methylphenyl)methyl]guanine, mp>300° C.;
8-amino-9-[(4-methoxyphenyl)methyl]guanine HCl salt, mp 238°–244° C. (dec);
8-amino-[(2-methoxyphenyl)methyl]guanine, HCl salt, mp>150° C. (dec); and
8-amino-[(3-methoxyphenyl)methyl]guanine, mp>300° C. (dec).

We claim:

1. A compound of the formula

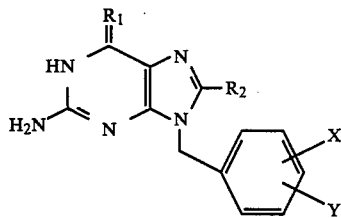

wherein $R_1$ is O or S; $R_2$ is bromine or NHR where R is hydrogen or $COR_5$ where $R_5$ is alkyl of one to four carbon atoms, aryl where aryl is phenyl unsubstituted or substituted by halogen, alkyl of one to four carbon atoms, alkxoy of one to four carbon atoms or trifluoromethyl, or arylalkyl where aryl is as defined above and alkyl is a carbon chain of up to four carbon atoms; Y is hydrogen and X and Y are each independently halogen, alkoxy of one to four carbon atoms, trifluoromethyl, hydroxy, CN, $SO_nR_3$, $COOR_3$, $NR_3R_4$ in which $R_3$ and $R_4$ are each independently hydrogen or alkyl of one to four carbon atoms and n is zero, one, two or three, or a pharmaceutically acceptable acid addition or base salt thereof.

2. A compound as claimed in claim 1, wherein $R_1$ is O or S; $R_2$ is bromine; Y is hydrogen and X and Y are each independently halogen, 1–4 carbon atoms, alkoxy of hydroxy or trifluoromethyl.

3. A compound as claimed in claim 2, wherein $R_1$ is O; Y is hydrogne and X and Y are each independently fluorine, chlorine, methoxy, hydroxy, carboxy, trifluoromethyl or $NR_3R_4$ wherein $R_3$ and $R_4$ are methyl.

4. A compound as claimed in claim 1, wherein $R_1$ is O or S; $R_2$ is $NH_2$; Y is hydrogen and X and Y are each independently halogen, atoms, alkoxy of 1–4 carbon COOH, hydroxy, trifluoromethyl or $NR_3R_4$ wherein $R_3$ and $R_4$ are methyl.

5. A compound as claimed in claim 4, wherein $R_1$ is O; $R_2$ is $NH_2$; Y is hydrogen, and X and Y are each independently fluorine, chlorine, methoxy, hydroxy, COOH, trifluoromethyl or $NR_3R_4$ wherein $R_3$ and $R_4$ are methyl.

6. A compound as claimed in claim 3 and being 8-bromo-9-[(4-chlorophenyl)methyl]guanine.

7. A compound as claimed in claim 3 and being 8-bromo-9-[(4-methoxyphenyl)methyl]guanine.

8. A compound as claimed in claim 3 and being 8-bromo-9-[(4-fluorophenylmethyl)guanine.

9. A compound as claimed in claim 3 and being 8-bromo-9-[(4-methylphenyl)methyl]guanine.

10. A compound as claimed in claim 3 and being 8-bromo-9-[(3,4-dichlorophenyl)methyl]guanine.

11. A compound as claimed in claim 5 and being 8-amino-9-[(4-chlorophenyl)methyl]guanine.

12. A compound as claimed in claim 5 and being 8-amino-9-[(4-fluorophenyl)methyl]guanine.

13. A compound as claimed in claim 5 and being 8-amino-9-[(4-methoxyphenyl)methyl]guanine.

14. A compound as claimed in claim 5 and being 8amino-9-[(3-methoxyphenyl) methyl]guanine.

15. A compound as claimed in claim 5 and being 8-amino-9-[(2-methoxyphenyl)methyl ]guanine.

16. A compound as claimed in claim 5 and being 8-bromo-9-[(2-methoxyphenyl)methyl]guanine.

17. A pharmaceutical composition for treating autoimmune diseases advantageously affected by selective toxicity to T-cells comprising an antiautoimmune effective cytotoxic tr T-cell amount of a compound according to claim 1 in admixture with a pharmaceutically acceptable carrier.

18. A method of treating autoimmune diseases in mammals advantaeously affected by selective toxicity to T-cells which comprises administering to such mammal in need thereof a cytotoxic to T-cell effective amount of a pharmaceutical composition according to claim 16.

* * * * *

UNITED STATES PATENT AND TRADEMARK OFFICE
CERTIFICATE OF CORRECTION

PATENT NO. : 4,748,177
DATED      : May 31, 1988
INVENTOR(S) : Jagadish C. Sircar, et al.

It is certified that error appears in the above—identified patent and that said Letters Patent is hereby corrected as shown below:

Column 12, line 28, change "bromo-9-[(4-fluorophenylmethyl]-guanine" to --bromo-9-[(4-fluorophenyl)methyl]guanine--.

Column 12, line 40, change "8amino-9-[(3-methoxyphenyl)methyl]guanine" to --8-amino-9-[(3-methoxyphenyl)methyl]-guanine--.

Column 12, line 6, change "1-4 carbon atoms, alkoxy of" to --alkoxy of 1-4 carbon atoms,--.

Column 12, line 14, change "atoms, alkoxy of 1-4 carbon" to --alkoxy of 1-4 carbon atoms,--.

Signed and Sealed this

Twenty-fifth Day of October, 1988

Attest:

DONALD J. QUIGG

*Attesting Officer*　　　　*Commissioner of Patents and Trademarks*